United States Patent [19]

Strickler

[11] 4,059,501
[45] Nov. 22, 1977

[54] AUTOMATED ELECTROPHORESIS UNIT

[75] Inventor: Allen Strickler, Fullerton, Calif.

[73] Assignee: Beckman Instruments, Inc., Fullerton, Calif.

[21] Appl. No.: 707,399

[22] Filed: Aug. 16, 1976

[51] Int. Cl.$^2$ .................. G01N 27/26; G01N 27/28
[52] U.S. Cl. ..................... 204/299 R; 204/180 S; 204/180 G; 204/300 R
[58] Field of Search ............... 204/180 S, 180 G, 299, 204/300

[56] References Cited

U.S. PATENT DOCUMENTS

| 3,133,009 | 5/1964 | Natelson | 204/180 S X |
| 3,764,513 | 10/1973 | Saravis | 204/299 |
| 3,896,021 | 7/1975 | Fosslien | 204/299 |

*Primary Examiner*—Arthur C. Prescott
*Attorney, Agent, or Firm*—Robert J. Steinmeyer; Robert R. Meads; Donald A. Streck

[57] ABSTRACT

Apparatus is disclosed for accomplishing electrophoresis in an automated manner. A supported electrophoretic medium, having been implanted with sample to be analyzed, is moved through a chamber wherein the electrophoresis takes place. The apparatus comprises an electrophoresis separation chamber containing a pair of elongated electrolyte wells, electrolyte contained within the wells, electrodes disposed within the electrolyte and connectable to an appropriate source of power, and a wicking arrangement communicating with each of the electrolyte wells to provide a continuous electrical contact zone. A moving belt arrangement is provided capable of moving support strips having the electrophoretic medium disposed thereon from one end of the separation chamber to the other while keeping one end of the strips in electrical contact with one wick and the opposite end in electrical contact with the second wick whereby a continuous electrical field is applied across the strips and electrophoretic medium as they move through the separation chamber and the electrophoresis separation is caused to take place. In the preferred embodiment, the strips containing the electrophoretic medium are releasably carried by a flexible backing material so that the strips can be moved into and through the separation chamber individually or in groups.

5 Claims, 6 Drawing Figures

AUTOMATED ELECTROPHORESIS UNIT

BACKGROUND OF THE INVENTION

The present invention relates primarily to clinical diagnostic apparatus and more particularly to apparatus for conducting diagnosis by electrophoresis.

Electrophoresis is a valuable diagnostic aid in a clinical laboratory which is limited in potential use because it requires many time consuming steps. Automation could greatly extend its application and permit wider use in routine patient screening. In electrophoresis, an electrophoretic medium, such as a gel or microporous membrane, has implanted into the surface thereof a sample material and (optionally) a reference material. A direct current electrical field is then applied across the medium. The various constituents (most often proteins) contained in the reference material (if used) and sample material will be caused to move in varying amounts across the medium as a result of this electrical field. After enough time has elapsed to cause migration over a sufficient distance to provide separation between the constituents capable of analysis, the electrical field is removed and a stain is applied to the medium which affects only the electrophoretically separated constituents therein. The medium itself is then caused to become transparent whereby the separated bands of stained, migrated reference and sample components will appear on a transparent background and can be analyzed by appropriate apparatus. By comparison of the sample bands to that of the reference bands, the composition of the sample material can be determined.

The actual electrophoresis process wherein the electrical field is applied is rather time consuming. Traditionally, this has been accomplished by affixing one or more pieces of support material containing the electrophoretic medium into a fixed chamber for the required time duration. The chamber is then opened and the batch removed and further processed. Once the processing of one or more samples within the chamber is started, the process must be completed before processing additional samples.

Patents typical of the prior art include that to Dwyer et al. (U.S. Pat. No. 3,594,263) disclosing a laminated sheet for electrophoresis comprising a flexible but stiff base sheet to which a separate microporous plastic membrane sheet is bonded. The laminated sheet is then used in a batch process electrophoresis chamber as shown in FIG. 1 of the Dwyer et al. patent.

In the patent to Saravis (U.S. Pat. No. 3,764,513), apparatus is shown employing a continuous backing member having a gel layer on its upper surface. A novel wicking arrangement is employed in a lid for the electrophoretic chamber whereunder a portion of the continuous backing member is disposed. With the lid lowered in position, the electrical field is established in the gel layer under the cover and a batch electrophoresis operation is conducted on that limited segment of the backing member. When the electrophoresis is complete, the used backing is moved out for analysis and a fresh portion assumes the active position under the lid. While employing a continuous backing member, the apparatus of Saravis still only discloses means for conducting batch process electrophoresis.

The patent to Hrdina (U.S. Pat. No. 3,303,120) teaches an improved batch process apparatus for paper electrophoresis wherein electrical contact is established by dipping the ends of the paper electrophoretic medium into electrolyte troughs during the electrophoresis process. To improve the waiting time until the next batch can be inserted, the apparatus of Hrdina employs means for moving the electrolyte trough away from contact with the ends of the paper and substituting a drip trough therefor. Drying air is then applied to dry the paper before its removal.

Therefore, it is an object of the present invention to provide apparatus for accomplishing the electrophoresis step per se on a continuing basis wherein the processing of additional samples can be started at any time while the processing of previously started samples can continue through to completion.

SUMMARY

The above object is achieved by the automated electrophoresis apparatus disclosed herein which comprises an elongated electrophoretic separation chamber defining a pair of elongated electrolyte wells wherein an electrolyte media is contained and having electrode means contained within the electrolyte media. An elongated, flexible, and continuous drive means is provided for carrying a plurality of transverse segments of plastic or the like coated with electrophoresis medium and mounted for movement longitudinally with respect to the separation chamber. Means are mounted adjacent the top of the separation chamber which are operable with lateral ends of the segments so as to make electrical contact with the electrolyte media. In the preferred embodiment, this is accomplished by wicks disposed between the lateral ends of the segments and the electrolyte media. A source of DC power is provided which is connected to the electrode means and operable to establish an electrical field transversely across the segments whereby electrophoretic separation can take place on the coated surface of the segments. Additionally in the preferred embodiment, the segments carrying the electrophoresis medium are releasably carried by a backing material. Means are provided for moving the backing material to an inlet of the separation chamber, including means for releasing individual segments disposed adjacent the inlet whereby a released strip will enter the separation chamber through the inlet to engage the drive means.

DESCRIPTION OF THE PREFERRED EMBODIMENT

Figure 1:
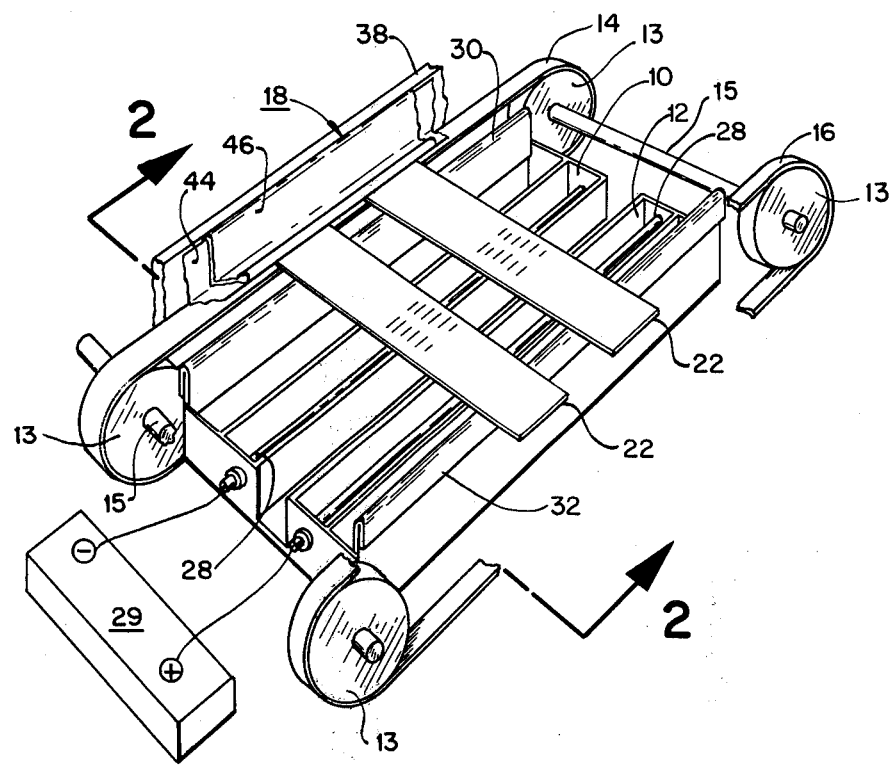
FIG. 1 is an orthographic, partial, cutaway view of the apparatus comprising the present invention.

Referring first to FIG. 1, a pair of elongated electrolyte wells 10 and 12 are provided in generally parallel spaced relationship as shown. A pair of continuous driven belts 14 and 16 are also disposed in parallel spaced relationship adjacent to wells 10, 12 and having wells 10, 12 therebetween. While numerous methods well known in the art could be used to operate driven belts 14 and 16, mounting the belts on pulleys 13 carried by shafts 15 in the manner shown wherein one of the shafts 15 is connected to a source of rotary power such as a motor or gearbox (not shown) has proved to provide satisfactory results. A pair of pressure members 18 and 20 are disposed with one pressure member 18 adjacent the top surface of driven belt 14 and a second pressure member 20 adjacent the top surface of driven belt 16 in a manner to be described in greater detail hereinafter. Driven belts 14, 16 and pressure members 18, 20 are adapted to grip and support transverse strips 22 having electrophoretic medium 24 thereon and to move the strips 22 through an electrophoretic zone existing between the ends of driven belts 14, 16 in a manner also to be described in greater detail hereinafter.

To form an electrophoretic chamber, each of the electrolyte wells 10, 12 is filled with an appropriate electrolyte solution 26 and has an electrode 28 immersed therein. A pair of wicks 30 and 32 is disposed in the electrolyte wells 10, 12 in such a manner that a support strip 22 being moved by the belts 14, 16 through the electrophoretic zone will be in constant contact with one edge of each of the adjacent wicks 30, 32. The other edge of each of the wicks 30, 32 is disposed within electrolyte solution 26 whereby the electrolyte solution 26 is drawn into the wicks by capillary action to provide electrical contact between the electrolyte solution 26 and the electrophoretic medium 24 on transverse strip 22 when DC power is applied to electrodes 28. In this regard, the electrodes 28 are adapted to be connected to a source of DC power 29 of sufficient magnitude to create an electrophoresis producing electrical field in an electrophoretic media.

Figure 2:
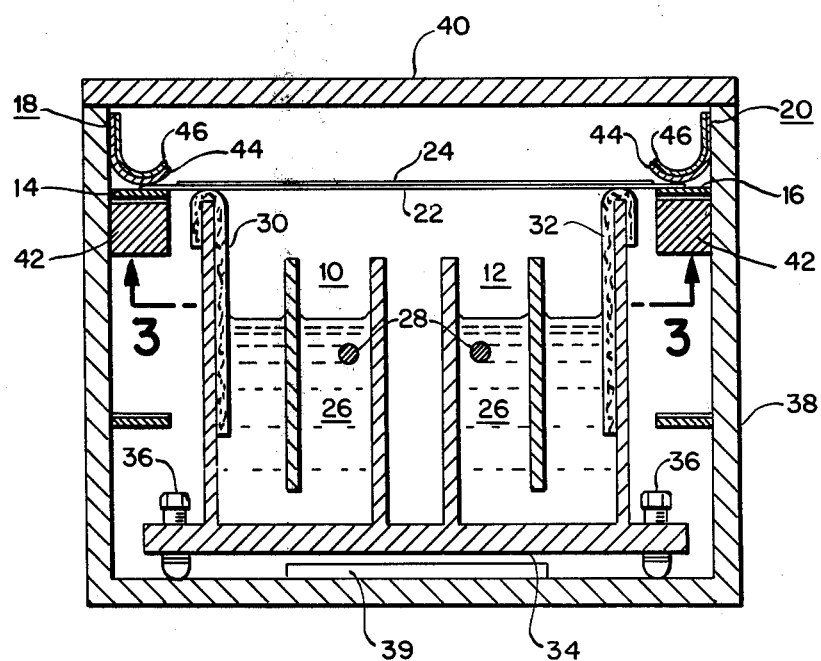
FIG. 2 is a cutaway end view of the apparatus of FIG. 1 along line 2—2 adding additional features omitted in FIG. 1 for clarity.

More specific details of the preferred embodiment of the present invention can be seen by referring to FIG. 2 in conjunction with FIG. 1. It is preferred that the electrolyte wells 10, 12 be integrally attached to a base 34 having leveling means 36 whereby the assembly can be placed in a level condition and the pressure of wicks 30, 32 against transverse strips 22 can be adjusted in a manner to be described later. It is also convenient and preferred to mount the base 34 having electrolyte wells 10, 12 thereon in an enclosure 38 having a lid 40. The enclosure 38 serves a number of functions. For one, it provides an appropriate means for mounting apparatus, to be hereinafter described, working in conjunction with driven belts 14, 16 and pressure members 18, 20, also mounted to enclosure 38, to move transverse strips 22 through the electrophoretic chamber. For another, enclosure 38 in conjunction with lid 40 provides a closed chamber wherein the temperature and humidity can be maintained at a constant and optimum level for the electrophoresis process by means 39 incorporating techniques well known in the art and which form no part of the present invention. As is well known, the electrophoretic medium must be maintained in a moist condition if electrophoresis is to take place in the presence of the electrical field. Of course, appropriate slots (not shown) must be provided in the walls of enclosure 38 to allow the entry and exit of the transverse strips 22 into and out of the electrophoretic chamber.

A pair of elongated pressure blocks 42 are mounted on the walls of enclosure 38 adjacent wicks 30, 32 and parallel to the top surface thereof. Pressure blocks 42 are spaced below the top of wicks 30, 32 a distance sufficient that when driven belts 14, 16 are moving along the tops of pressure blocks 42 and supported thereby, the top surfaces of driven belts 14, 16 will be substantially level with the top surface of wicks 30, 32.

The previously referred to pressure members 18, 20 are attached to opposite sides of enclosure 38 in a manner which will allow them to bear against the top of driven belts 14, 16 under slight pressure along the entire surface thereof. The pressure members 18, 20 each comprise a material 44 having a low coefficient of friction (as by employing a thin sheet of polytetrafluoroethylene) disposed adjacent the driven belts 14, 16. The pressure members 18, 20 further comprise a spring means 46 disposed to urge the low friction material 44 against the surface of driven belts 14, 16. In the preferred embodiment of FIG. 2, spring means 46 comprise a generally "L" shaped spring member having polytetrafluoroethylene on one surface thereof. One side of the "L" is attached to the wall of enclosure 38, with the other side of the "L" disposed to urge transverse strips 22 against the tops of belts 14, 16. The previously referred to polytetrafluoroethylene is disposed on the surface of the spring adjacent the top of the transverse strips 22.

When a strip 22 is inserted through the slot (not shown) in enclosure 38, it will be gripped between the top surface of driven belt 14 and pressure member 18 along one end and between driven belt 16 and pressure member 20 on the opposite end. Driven belts 14, 16 should have the upper surface thereof of a material or texture having a high coefficient of friction. This causes transverse strips 22 to be gripped along the bottom surface by the upper surface of driven belts 14, 16 while the upper surface of strips 22 can slide easily along the low friction material 44. In this manner, strips 22 can be moved slowly and steadily through the electrophoretic zone with wicks 30, 32 bearing against the bottom surface thereof to support an electrical field in the electrophoretic medium 24 between wicks 30 and 32. Since pressure blocks 42 are attached to the walls of enclosure 38, and base 34 is movable vertically up and down by means of leveling means 36, the pressure of wicks 30, 32 against the bottom of strips 22 can be adjusted for proper operation by moving base 34 and wicks 30, 32 up or down as necessary within chamber 38 using leveling means 36. Thus, electrophoresis can take place in the entire electrophoretic zone or chamber which exists between one end of wicks 30, 32 and the opposite ends thereof.

For proper electrophoresis, the conditions as to temperature, humidity, and the electrical field must be maintained in a steady state. Accordingly, it is preferred that certain attributes be possessed by the material and design of the apparatus. Electrodes 28 should be of an inert material as, for example, platinum wire. To provide an equal potential throughout the length of the electrophoretic zone, it is preferred that the electrodes 28 extend from one end of the electrolyte wells 10, 12 to the other. Superior results will be obtained if baffles 48 are inserted lengthwise in each of electrolyte wells 10, 12 to divide them into two compartments whereby electrolysis products formed at the electrodes 28 in one compartment will be kept from coming in contact with and thereby contaminating wicks 30, 32 in the separated compartment. Baffles 48 are spaced away from the bottom of electrolyte wells 10, 12 to allow the passage of electrolyte solution 26 thereunder.

Figure 3:
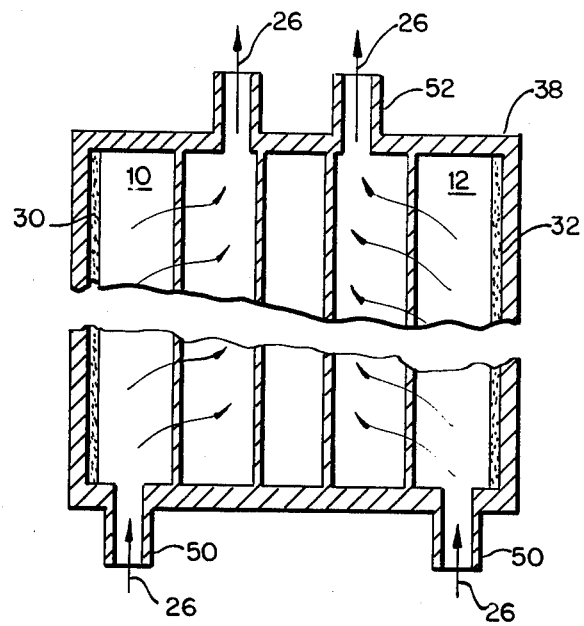
FIG. 3 is a cutaway top view of the electrophoretic separation chamber of FIG. 2 along line 3—3 showing the preferred flow path for circulating the electrolyte therethrough.

Since it is also advantageous to recirculate the electrolyte solution 26 to maintain a constant electrolyte concentration, the recirculation can be put to additional use. If the recirculation path is constructed as shown in FIG. 3, with the inlet ports to electrolyte wells 10, 12 adjacent the wall thereof containing wicks 30, 32 and the outlets 52 are disposed adjacent the center walls, the electrolyte solution 26 will enter and sweep past the electrodes 28 away from the wicks 30, 32 and exit through outlets 52. This action assures that electrolysis products formed at the electrodes 28 will not reach the wicks 30, 32 where altered pH or ionic composition could adversely affect the electrophoresis process. Thus, a novel means for electrode rinsing is incorporated into the apparatus.

When such recirculating means are used, it is possible to create a shunt path for current through the recirculating means which will shunt current from the normal and desired path represented by the electrolyte wells 10, 10, the wicks 30, 32, and the electrophoretic medium 24. To avoid excessive shunting of the electrical current through the external circulation paths, the streams feeding inlets 50 and draining from outlets 52 should not join each other at positions too close to the electrolyte wells 10, 12. To further minimize shunting of current, the tubing in the shunting paths can be made of a relatively small internal diameter. Other techniques for restricting and/or interrupting current flow through the recirculation paths and pumping means therefor will be adaptable by those skilled in the art.

Figure 4:
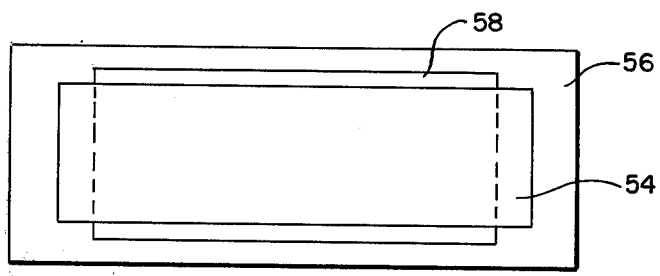
FIG. 4 is a top view of one method for supporting an electrophoresis medium for use in the present invention.
Figure 5:
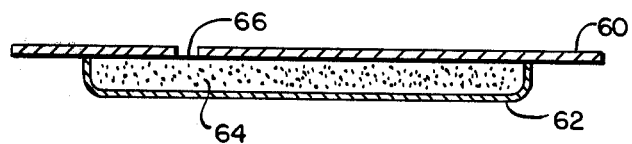
FIG. 5 is a side elevation of a second method for supporting an electrophoresis medium for use in the present invention.

Referring now to FIGS. 4 and 5, two possible embodiments for combining the electrophoretic medium with the transverse strip are disclosed. In the embodiment of FIG. 4, the electrophoretic medium is a membrane 54 attached to a frame 56 of plastic or the like having a rectangular opening 58 therein. The ends of the membrane 54 are attached to the frame 56 by heat-sealing, cement, or any of the other techniques well known in the art. Optionally, the rectangular opening 58 could be omitted. In the embodiment of FIG. 5, shown in cross section, a plastic strip 60 is provided having an enclosure 62 along one surface thereof. The electrophoretic medium in the form of a gel 64 is disposed within enclosure 62 as by casting. An opening 66 is provided in the plastic strip 60 through which sample may be applied into the gel. Obviously, any plastic material disposed between the wicks and the electrophoretic medium must be such as to provide an electrical path.

Figure 6:
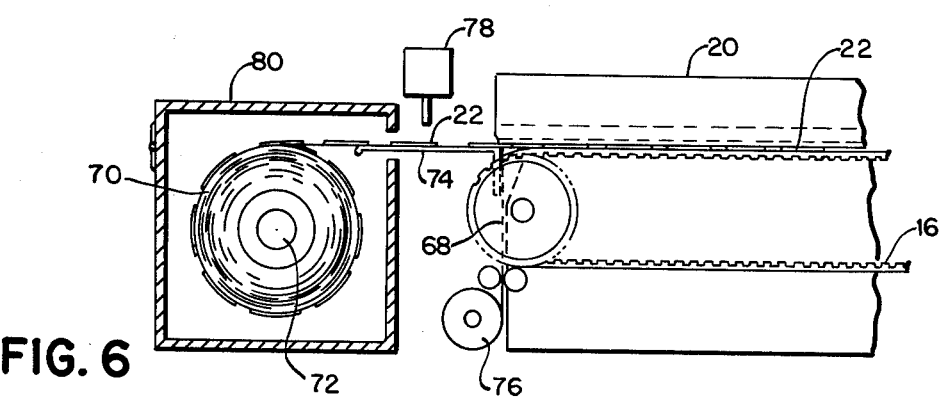
FIG. 6 is a partial side view of the apparatus of FIGS. 1 and 2 adapted to receive samples in an automated manner.

To adapt the apparatus of the present invention for the automatic feeding of a plurality of separated transverse strips 22 containing electrophoretic medium 24 for use in either manual or automated operations, the additional apparatus of FIG. 6 can be appended. A plurality of strips 22 are releasably attached, as with adhesive, in spaced relationship to a flexible backing member 68. The flexible backing member 68 containing transverse strips 22 is then wound onto a supply reel 70 which is rotatably mounted on a supply shaft 72. The flexible backing member 68 is passed across the top surface of an input plate 74 having a straight edge adjacent the input to the electrophoretic chamber in a manner to be hereinafter described in greater detail. The flexible backing member is then angled down substantially normal to the path of the strips 22 into the electrophoretic chamber and wound onto a takeup reel 76. A constant driving force can be applied to flexible backing member 68 by passing it between a drive roller 75 and idler roller 77 as shown. With this apparatus disposed as shown in FIG. 6, when drive roller 75 and idler roller 77 grip and move flexible backing member 68 forward and takeup reel 76 is operated to wind flexible backing member 68 thereon, the backing member 68 and transverse strips 22 will move forward in unison to the edge of input plate 74 which is disposed with a horizontal edge normal to belts 14, 16. As flexible backing member 68 bends over this edge of plate 74 from its horizontal motion to its vertically downward motion toward takeup reel 76, the adhesive holding strips 22 to flexible backing member 68 is so chosen as to release in a peeling fashion, thereby allowing transverse strips 22 to continue in the horizontal direction as flexible backing member 68 is progressively removed therefrom. The distance between the edge of input plate 74 and the point at which the strips 22 are gripped between driven belts 14, 16 and pressure members 18, 20 should be sized such that strips 22 will be fully released from flexible backing member 68 at substantially the same time as they are gripped and moved into the electrophoretic chamber by driven belts 14, 16 and pressure members 18, 22.

Obviously, automated sample inserting apparatus 78 and a strip conditioning chamber 80 surrounding supply reel 70 to maintain strips 22 at the proper temperature and humidity by techniques well known to those skilled in the art could be provided to further enhance the operation of the apparatus.

Having thus described my invention, I claim:
1. Automated electrophoresis apparatus comprising:
   a. an elongated electrophoretic separation chamber having an inlet and an outlet and including a pair of electrolyte wells;
   b. electrolyte contained within said wells;
   c. means for moving a strip of electrophoretic medium through said separation chamber from said inlet to said outlet;
   d. electrode means disposed in electrical contact with said electrolyte in said wells and adapted to be connected to a source of d.c. power;
   e. a pair of wicks disposed one to each of said wells to provide constant electrical contact between said electrolyte in said wells and the electrophoretic medium as it moves through said chamber whereby an unchanging electrical field will be established in a portion of the electrophoretic medium while it is moving through said chamber;
   f. a flexible backing material releasably carrying strips of electrophoretic medium;
   g. an input plate in parallel relationship with said moving means and having an edge adjacent the input of said chamber whereby said flexible backing material can be moved across said plate carrying said strips of electrophoretic medium toward said inlet and said moving means then bend around said edge to a new direction substantially normal to said moving means to cause said strips of electrophoretic medium to be released from said flexible backing material and continue into said inlet of said electrophoretic separation chamber to engage said moving means; and,
   h. means for moving said flexible backing material across said input plate in the manner described.
2. Automated electrophoresis apparatus as claimed in claim 1 wherein additionally:
   a. said contact means comprises a pair of wicks disposed one to each of said wells; and, b. each of said electrolyte wells has an inlet disposed adjacent said wick and an outlet disposed away from said wick, said inlets and outlets including connecting means adapted to be operably connected to means for recirculating said electrolyte whereby an electrode rinsing action by the movement of said electrolyte across said electrodes and away from said wicks will be created within said electrolyte wells.

3. Automated electrophoresis apparatus as claimed in claim 2 wherein:
said connecting means includes means for suppressing the shunting of electrical current through said recirculating means via paths external to the path represented by said electrolyte in said electrolyte wells, said wicks and said electrophoretic medium.

4. Automated electrophoresis apparatus as claimed in claim 1 and additionally comprising:
 a. an enclosure surrounding said electrophoretic separation chamber and including means for maintaining a controlled environment therein to maintain the electrophoretic medium under conditions favorable for electrophoresis, said enclosure further carrying said moving means; and,
 b. a base disposed within said enclosure and carrying said electrolyte wells and said contact means, said base including leveling means whereby the position of said base and said contact means within said enclosure can be changed to assure constant electrical contact between said contact means and the electrophoretic medium as the electrophoretic medium is carried through said electrophoretic separation chamber.

5. Automatic electrophoresis apparatus comprising:
 a. an elongated electrophoretic separation chamber having an inlet and an outlet and including a pair of electrolyte wells;
 b. electrolyte contained within said wells;
 c. means for moving a transverse strip of electrophoretic medium through said separation chamber from said inlet to said outlet;
 d. electrode means disposed in electrical contact with said electrolyte in said wells and adapted to be connected to a source of d.c. power;
 e. means for providing constant electrical contact between said electrolyte in said wells and the electrophoretic medium as it moves through said chamber whereby an unchanging electrical field will be established in a portion of the electrophoretic medium while it is moving through said chamber;
 f. a backing material releasably carrying strips of electrophoretic medium; and,
 g. means for moving said backing material to said inlet of said chamber including means for releasing individual strips of the electrophoretic medium disposed adjacent said inlet whereby a released strip will enter said inlet to engage said moving means.

* * * * *